(12) United States Patent
Bobo, Sr. et al.

(10) Patent No.: US 9,232,921 B2
(45) Date of Patent: Jan. 12, 2016

(54) SYSTEM AND METHOD FOR INTRACRANIAL ACCESS AND MONITORING

(75) Inventors: Donald E. Bobo, Sr., Fountain Valley, CA (US); James Gerg, Lake Forest, CA (US)

(73) Assignee: InnerSpace Medical, Inc., Tustin, CA (US)

( * ) Notice: Subject to any disclaimer, the term of this patent is extended or adjusted under 35 U.S.C. 154(b) by 576 days.

(21) Appl. No.: 12/792,650

(22) Filed: Jun. 2, 2010

(65) Prior Publication Data

US 2010/0241132 A1 Sep. 23, 2010

Related U.S. Application Data

(62) Division of application No. 10/855,159, filed on May 26, 2004, now Pat. No. 7,780,679.

(60) Provisional application No. 60/475,056, filed on May 30, 2003.

(51) Int. Cl.
*A61M 1/00* (2006.01)
*A61B 5/00* (2006.01)
(Continued)

(52) U.S. Cl.
CPC ............... *A61B 5/6864* (2013.01); *A61B 5/031* (2013.01); *A61B 17/1695* (2013.01); *A61B 19/201* (2013.01); *A61B 5/01* (2013.01);
(Continued)

(58) Field of Classification Search
CPC .... A61B 5/6864; A61B 5/031; A61B 5/6868; A61B 17/1695; A61B 2018/00446; A61B 2019/208; A61M 25/003; A61M 25/0032; A61M 2025/0037; A61M 2025/0086; A61M 27/006; A61M 39/0247; A61M 2039/0235; A61M 2039/0214; A61M 2039/025; A61M 2210/0687
USPC ........................... 606/139, 108; 604/174, 175
See application file for complete search history.

(56) References Cited

U.S. PATENT DOCUMENTS 4,438,773 A * 3/1984 Letterio .................... 600/561
4,445,893 A * 5/1984 Bodicky ................ 604/165.04
(Continued)

FOREIGN PATENT DOCUMENTS

| GB | 2 330 078 A | 4/1999 |
|---|---|---|
| GB | 2 342 583 A | 4/2000 |
| WO | WO96/02297 A1 | 2/1996 |

OTHER PUBLICATIONS

European Patent Office, Supplementary European Search Report dated Jun. 8, 2010 in European Patent Application No. 04753596.8-2310/1633233, 6 pages.
(Continued)

*Primary Examiner* — Julian W Woo
*Assistant Examiner* — Shaun L David
(74) *Attorney, Agent, or Firm* — Inskeep IP Group, Inc.

(57) ABSTRACT

A system and method for intracranial access is disclosed. In particular, a drill stop is shown providing a way to control the penetration of a drill bit as an access hole into the brain is being formed. Access to a desired location is achieved using a catheter guide device. Also disclosed is a mechanism by which multiple diagnostic and treatment devices can be placed at a desired location in brain tissue without the need for more than one access hole. A drainage catheter is disclosed with a mechanism to allow both drainage and to allow intracranial pressure measurement.

11 Claims, 6 Drawing Sheets

(51) Int. Cl.
   *A61B 5/03* (2006.01)
   *A61B 17/16* (2006.01)
   *A61B 19/00* (2006.01)
   *A61B 5/01* (2006.01)
   *A61B 5/1473* (2006.01)

(52) U.S. Cl.
   CPC ........ *A61B 5/1473* (2013.01); *A61B 2019/303* (2013.01); *A61B 2019/464* (2013.01)

(56) References Cited

U.S. PATENT DOCUMENTS

| | | | |
|---|---|---|---|
| 4,646,752 A | | 3/1987 | Swann et al. |
| 4,681,103 A | | 7/1987 | Boner et al. |
| 4,993,425 A | * | 2/1991 | Kronberg ............... 600/561 |
| 5,054,497 A | * | 10/1991 | Kapp et al. ............... 600/561 |
| 5,391,152 A | * | 2/1995 | Patterson ............... 604/165.04 |
| 5,713,858 A | * | 2/1998 | Heruth et al. ............ 604/288.02 |
| 5,766,249 A | * | 6/1998 | Griffith ............... 600/30 |
| 5,927,277 A | * | 7/1999 | Baudino et al. ............... 600/386 |
| 5,990,382 A | * | 11/1999 | Fox ............... 623/16.11 |
| 6,018,084 A | | 1/2000 | Nakada et al. |
| 6,018,094 A | * | 1/2000 | Fox ............... 606/191 |
| 6,572,624 B2 | * | 6/2003 | U et al. ............... 606/130 |
| 6,623,490 B1 | * | 9/2003 | Crane et al. ............... 606/108 |
| 6,673,022 B1 | * | 1/2004 | Bobo et al. ............... 600/561 |
| 7,094,234 B1 | * | 8/2006 | Lennox ............... 606/49 |
| 7,637,915 B2 | * | 12/2009 | Parmer et al. ............... 606/108 |
| 7,780,679 B2 | * | 8/2010 | Bobo et al. ............... 606/108 |
| 2003/0040753 A1 | | 2/2003 | Daum et al. |
| 2003/0130651 A1 | * | 7/2003 | Lennox ............... 606/21 |

OTHER PUBLICATIONS

United States Patent and Trademark Office, Notice of Allowance mailed Jan. 13, 2010 in U.S. Appl. No. 10/855,159, 7 pages.
United States Patent and Trademark Office, Final Office Action mailed Jan. 23, 2009 in U.S. Appl. No. 10/855,159, 9 pages.
United States Patent and Trademark Office, Office Action mailed Jul. 24, 2008 in U.S. Appl. No. 10/855,159, 8 pages.
WIPO, U.S. International Preliminary Examining Authority, International Preliminary Report on Patentability mailed Dec. 28, 2006 in International Patent Application No. PCT/US04/16794, 3 pages.
WIPO, U.S. International Search Authority, International Search Report and Written Opinion mailed Sep. 18, 2006 in International Patent Application No. PCT/US04/16794, 7 pages.

* cited by examiner

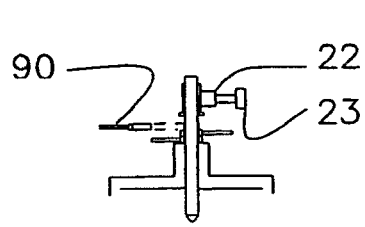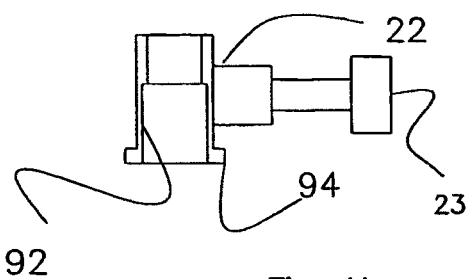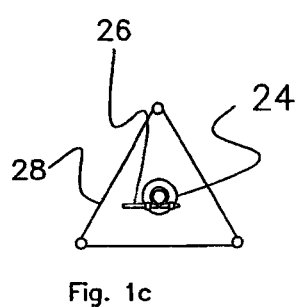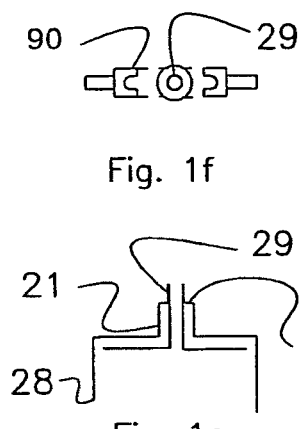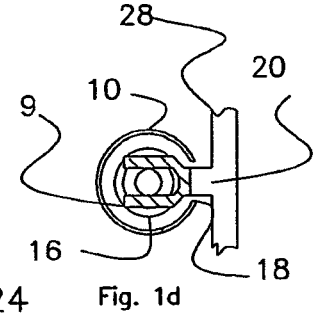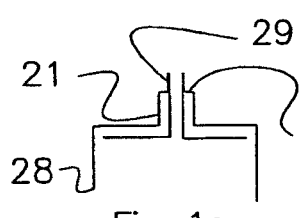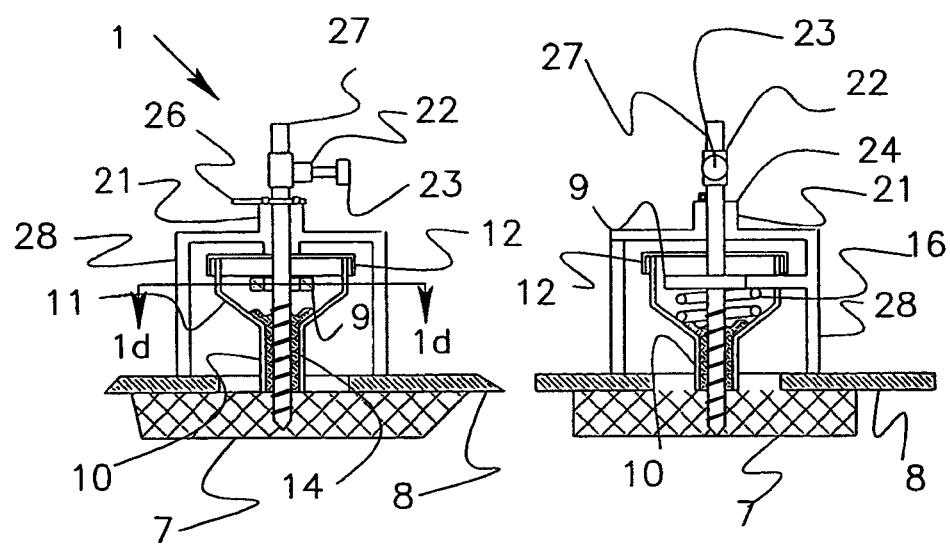

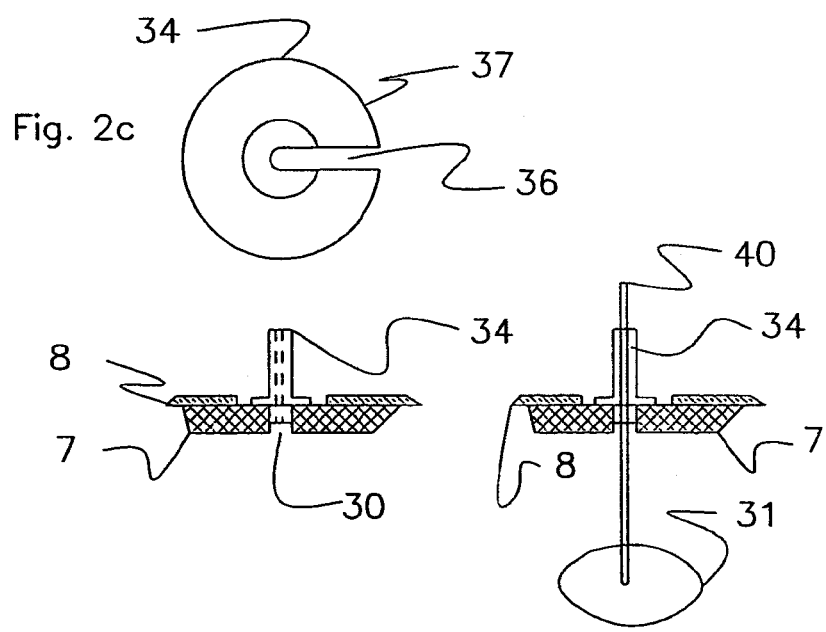

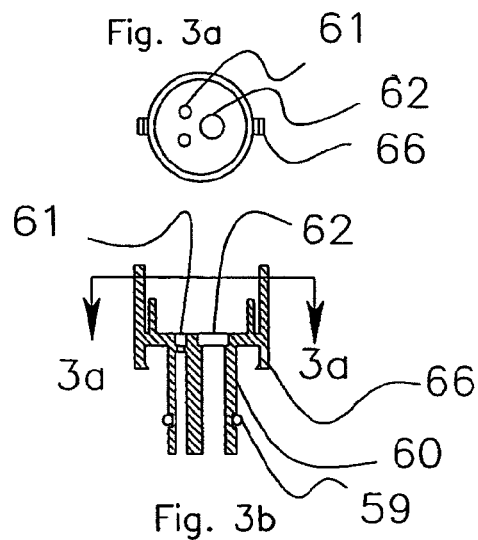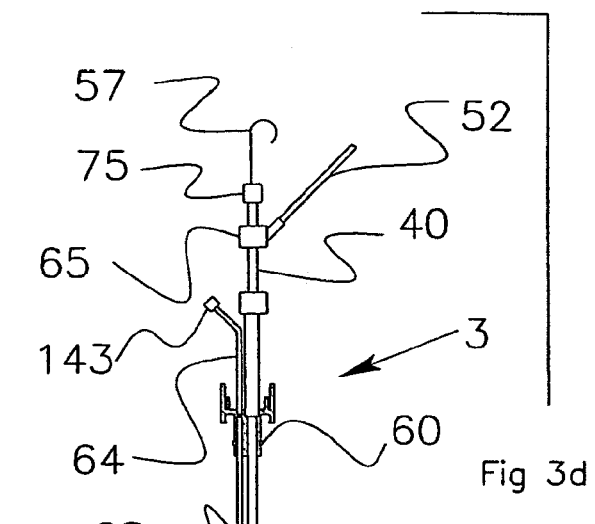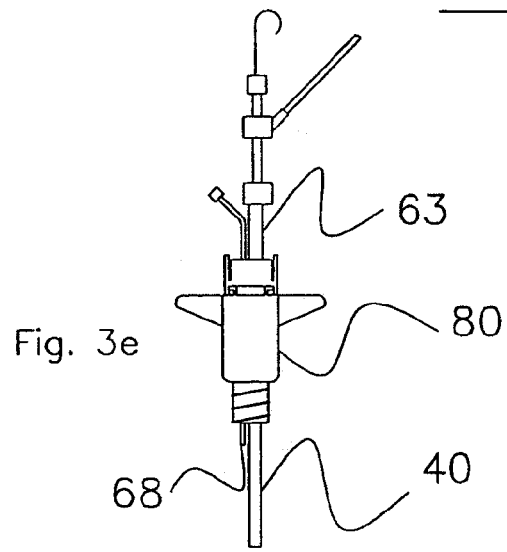

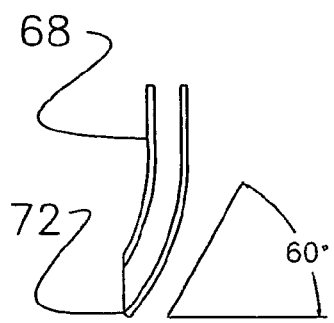
Fig. 4d
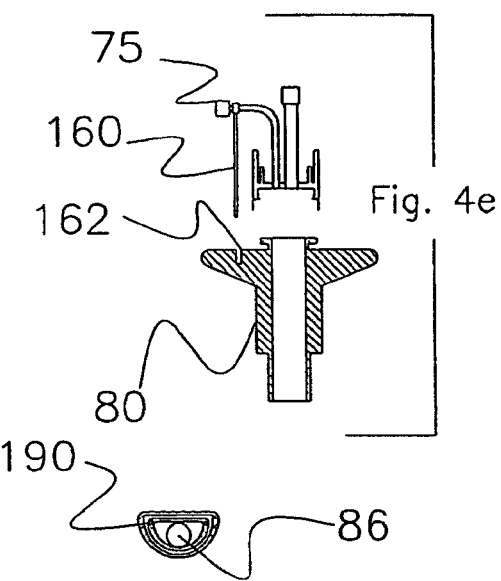
Fig. 4e
Fig. 4c
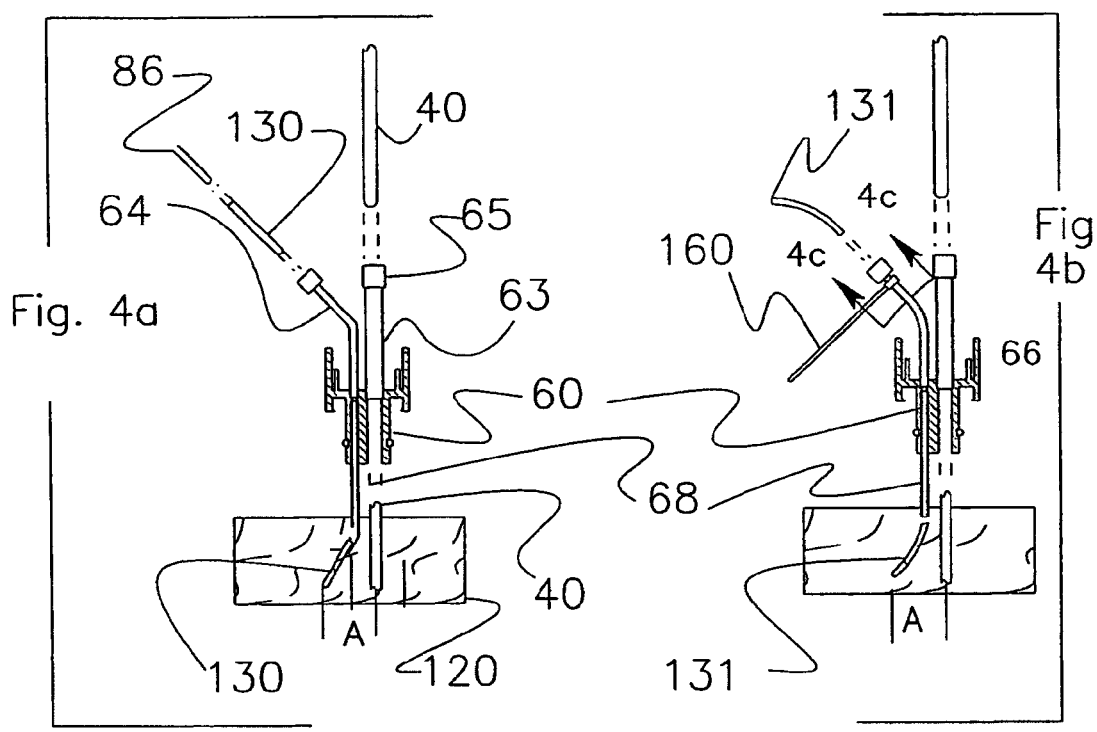
Fig. 4a
Fig 4b

SYSTEM AND METHOD FOR INTRACRANIAL ACCESS AND MONITORING

CROSS REFERENCE TO RELATED APPLICATIONS

This application is a divisional of U.S. patent application Ser. No. 10/855,159, filed May 26, 2004 now U.S. Pat. No. 7,780,679, entitled System And Method For Intracranial Access And Monitoring, which is related to and claims priority from U.S. provisional application Ser. No. 60/475,056 filed on May 30, 2003 entitled System And Method For Intracranial Access, both of which are hereby incorporated herein by reference.

BACKGROUND OF THE INVENTION

Systems and methods are disclosed which are directed to intracranial access for diagnostic as well as therapeutic indications, specifically, an access system, a ventricular catheter, a bolt insert assembly with a probe guide and an introducer.

Access System: Drilling a Hole.

Twist drill devices presently used to drill a hole in the skull have two shortcomings. One shortcoming is an inability to stop drilling as soon as the drill bit has passed through the skull. A second shortcoming relates to the process of removing the bone material generated by drilling a hole. The bone material must be carefully removed from the drill site around the drill hole in a manner that minimizes the material that falls back in the drill hole. It is important that the drill bit is stopped immediately after the drill bit passes through the skull. Any significant movement of the drill bit beyond the skull will traumatize the brain. Currently, a hand drill is used to drill a hole in the skull. A drill stop is placed on the bit to act as a safety device. It prevents the forward movement of the bit beyond a defined point and thereby prevents the drill bit from inadvertently plunging into the brain as a result of continuing pressure on the drill after the hole is completed. The drill stop cannot be precisely located on the bit in a manner that causes the drill to stop forward motion as soon as it passes through the skull. The inability to precisely place the drill stop relates in part to the fact that the surgeon does not know the exact thickness of the skull. The drill stop allows the surgeons to partially drill through the skull without risk of plunging. When the hole is nearly complete, the drill stop is loosened and backed off to allow additional forward movement so the bit can pass through the skull. The surgeon continues to drill very carefully until he senses that the tip of the drill bit has passed through the bone. The sense of when the bit has passed through the skull is not precise and therefore, the distance the drill bit moves beyond the bottom of the skull is not precise. Consequently, the drill bit may move more deeply into the brain than desired. The present invention provides a device that stops the drill bit as soon as it exits the skull and does so in a manner that requires no specialized skill on the part of the doctor.

Access System: Removing Bone Material Generated by Drilling.

A second problem in current methods used to drill a hole in the skull relates to the removal of the bone material that accumulates around the drill bit. The bone material removed from the drill hole forms a sizable anthill-like pile adjacent to the hole. At the end of the drilling process, the doctor removes much of the bone material with a gauze cloth and then removes the remaining material by rinsing the surrounding area. Some of the bone material is flushed into the drill hole in this process. The present invention collects bone material as it is produced, thus preventing an accumulation of bone material around the drill hole. Removing the bone material as it is produced eliminates the need to swab and rinse the drill site.

Access System: Targeting a Ventricle.

Once the hole is created, the surgeon typically attempts to insert a ventricular catheter through the hole and into a ventricle of the brain. The anatomy of the skull and brain is such that an imaginary line perpendicular to the skull at the point of a drill hole will pass through a ventricle. The surgeon aims the catheter at the ventricle by orienting the catheter as best he can so it enters the drill hole perpendicular to the skull. If the catheter is not properly orientated, the catheter will miss the ventricle and require that the surgeon withdraw the catheter and try again. Several prior art devices have been described that direct the angle of entry of the drill bit and or the catheter. The devices are cumbersome enough that they have not been widely adopted. The present invention presents a device that directs the angle of entry of the catheter and does so in a simple-to-use manner.

Therapy: A Catheter with a Standard Drainage Capability.

One important aspect of any ventricular catheter is that of providing a multiplicity of radial holes that lead to a drainage lumen. Multiple holes reduce the likelihood that brain tissue or blood clots will block the flow of cerebral spinal fluid (CSF) into the drainage lumen. Prior art air-column ventricular catheters are constrained in the number of radial holes that can be offered. Generically, an air-column catheter consists of a flaccid bladder mounted to a catheter wherein an air column extends from the bladder to an external transducer. The bladder volume responds to changing ICP according to $P_1V_1=P_2V_2$. The bladder used by the prior art air-column is an external sleeve, which is essentially a tube with its ends bonded to the catheter body. The tube-shaped bladder covers the catheter body beneath it. The bladder length required by the system for proper operation is such that the bladder covers most of the catheter body that resides in a ventricle. The room available for the placement of radial drainage is therefore very limited. The predicate air-column catheter presents 4 radial holes vs. the 10-to 15 radial holes provided in a standard ventricular catheter. An air-column catheter with a sleeve bladder, therefore, has an inferior drainage capability compared to a standard ventricular catheter now used.

In the present invention, the bladder is mounted within the catheter. By placing the bladder within the catheter, the entire surface of the catheter body in the ventricle is available to provide radial hole access to the main drainage lumen and thereby provide the same drainage capability as a standard catheter.

Therapy Access: Placement of Monitoring Probes and a Drainage Catheter Through One Drill Hole.

In the course of managing patients, some neurosurgeons find it helpful to measure parameters such as tissue oxygen. A three-parameter device is presently available that provides access for ICP, O2 and temperature probes. The device does not include the ability to drain CSF. Removing CSF is an important therapeutic procedure in that it provides additional volume within the skull into which traumatized brain can expand. At this time, a first hole is drilled into the skull for placement of the three-parameter device. A second hole is then drilled in the skull to provide access for a ventricular catheter. It is highly desirable to provide a single-hole system that can provide access for multiple monitoring probes such as ICP, oxygen and temperature and also provide access for a ventricular catheter. Such a system would avoid the need to drill a second hole.

Oxygen probes have a very specific placement requirement. They must be placed in undisturbed tissue to obtain accurate values. In the prior art, the ICP, O2 and temperature sensors are placed straight down into the brain through three parallel guide tubes. The oxygen probe is isolated from tissue disturbed by the other two probes by placing the oxygen probe deeper into the brain than the other sensors. Since a ventricular catheter extends all the way through the brain to a ventricle, a system that contemplates the placement of a ventricular catheter and oxygen probe through the same drill hole must cause the oxygen probe to move laterally away from the track of the ventricular catheter. As will be disclosed, the present invention provides an element within a bolt that moves a probe laterally away from the track of the ventricular catheter. Probes vary in their diameter and physical properties and may not interact well with an element designed to move the probe to one side. The present invention uses an introducer with well-defined pushability and memory characteristics to carry a probe into the brain, thus ensuring that all probes can successfully be moved into undisturbed brain tissue.

The introducer can be laterally displaced by placing a deflector at the distal end of the guide tube. It can also be displaced by use of a precurved introducer. Upon exiting a guide tube, the memory of the precurved introducer causes the introducer to move away from the guide tube in an arc. A system that could place four functions, namely, O2, temperature, ICP and a drainage catheter, through a single skull hole would address a clear clinical need by avoiding the need to drill a second hole. The present invention allows all four functions to be placed in the brain through one drill hole.

Adding a Third Parameter.

At this time, neurosurgeons are considering the use of other probes to properly manage the patient. Flow probes, for example, are currently being used to track changes in blood flow rates. In order to enable the disclosed system to accept an additional probe without changing the diameter of the hole drilled in the skull, the oxygen probe is placed in an introducer that has an integrated temperature sensor. Temperature is a necessary input into the oxygen instrument since the oxygen value must be interpreted as a function of temperature. Combining oxygen and temperature into an introducer frees one probe port for use by another parameter such as flow and does so without increasing the size of the bolt and its companion drill hole.

OBJECTS AND ADVANTAGES

One object of the invention is to stop the forward movement of a twist drill bit as soon as it passes through the skull and to do so without requiring skill on the part of the surgeon. The invention precisely stops the drill bit and does so without any expertise on the part of the surgeon.

A second objective of the invention is to collect bone material removed from a drill hole as it is produced and thereby avoid an accumulation of bone material that must be removed from the drill site by swabbing and rinsing.

A third objective of the invention is to provide a device that will guide the path of a ventricular catheter as it enters the brain.

A fourth objective of the invention is to provide an air-column catheter with a sufficient number of radial holes leading to a drainage lumen that they provide an inflow area typical of a standard catheter.

A fifth objective of the invention is to incorporate the ability to pass multiple monitoring probes plus a ventricular catheter through a single bolt and thereby avoid the need to drill a separate hole for a ventricular catheter. This objective requires that probes sensitive to disturbed tissue be moved away from the ventricular catheter track and into undisturbed brain tissue.

A sixth objective is to accomplish the preceding objectives within the confines of a diameter typical of the ventricular catheters now used.

A seventh objective of the invention to achieve a low cost product by replacing some conventional design elements with design elements that are less expensive to manufacture.

BRIEF SUMMARY OF THE INVENTION

A cranial access system is disclosed that provides a precision drill stop, collects bone material removed from the skull, orients the axis of the drill hole so that it is perpendicular to the skull and provides a catheter guide that, when placed in the oriented drill hole, will guide the path of a ventricular catheter toward a ventricle.

An air-column ventricular catheter is disclosed that has its bladder mounted inside the catheter body to thereby make the entire outer surface of the catheter available for the formation of radial drill holes. The drainage holes provide a drainage capability similar to that of conventional ventricular drainage catheters and do so in a standard size catheter.

A bolt and insert system is disclosed that makes possible the introduction of four functions into the brain through one drill hole. Two of the functions, ICP sensing and CSF drainage, are incorporated into a catheter that is passed through a bolt. The bolt provides insertion ports for two other parameters, such as oxygen and temperature. Some parameters must be placed in undisturbed brain tissue to function properly. The system provides the ability to move such a probe away from the track of the ventricular catheter and into undisturbed tissue. The probes are placed in an introducer to provide a consistent maneuverability characteristic to the various probes that might be used. One version of the introducer has a temperature sensor integrated into the body of the introducer. It frees up one probe port and thereby makes it possible to introduce another parameter.

BRIEF DESCRIPTION OF THE DRAWINGS

FIG. 1a-h show a bone collection and drill stop system.

FIGS. 2a and 2b show a ventricular catheter guide.

FIG. 3a-c show a bolt insert system that receives monitoring probes.

FIGS. 3c-d show the bolt insert system assembled on a ventricular catheter.

FIG. 3e shows the placement of the assembly into a bolt that is screwed into the skull.

FIGS. 4a, 4b, 4c and 4d show the insertion of an introducer into the brain in a manner that moves an oxygen probe away from the track of a ventricular catheter.

DETAILED DESCRIPTION OF THE INVENTION

Figure 5G:
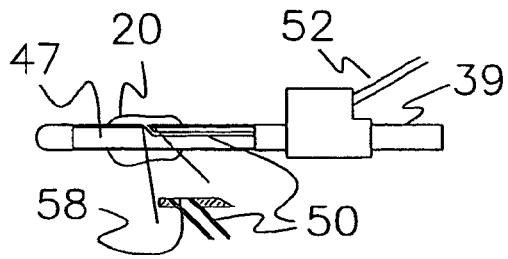
FIG. 5g shows an air tube in communication with a bladder mounted on the outside of the catheter.

FIGS. 1a through 1h present a bone collection and drill stop assembly 1. FIG. 1a shows a partial cross section of the assembly. FIG. 1b shows the same assembly rotated 90 degrees. FIG. 1c shows a plan view of a tripod assembly 1. FIG. 1d provides a section 1d-1d that shows a fork element 9 in the tripod that is the upper stop of a spring 16. The spring causes the bone collection device to stay in constant contact with the skull.

Precision Drill Stop.

A tripod 28 is placed on a scalp 8 that has been retracted to expose skull bone 7. The tripod has a drill guide 21 through which a drill 27 passes. The tripod drill guide causes the drill guide axis to be aligned perpendicular to an imaginary plane that is tangential to the skull at the drill hole site. The anatomy of the head is such that the axis of the drill guide 21 passes through a ventricle. The forward motion of the drill 27 is constrained by a drill stop 22, which is fixed to the drill bit 27 by a socket screw 23. The drill stop 22 allows the surgeon to drill into the skull bone without the risk of having the drill 27 inadvertently passing through a completed hole and plunging into the brain. The top surface of a drill stop 22 contact surface 24 is shown in FIG. 1c. It holds a pin 26. The surgeon senses when the drill bit tip 27 first exits the skull as the torque required to rotate the drill increases noticeably. At this time, the drill stop 22 is loosened and allowed to come down to rest on top of pin 26. The diameter of the pin 26 is identical to the length of the conical tip of the drill bit. The drill stop 22 is then tightened and the pin 26 removed. The drill bit is now free to move downward for a distance equal to the diameter of the pin at which time it contacts a drill stop contact surface 24. Since the diameter of the pin 26 is the same as the length of the tip of the drill bit 27, he distance that the drill bit 27 will pass through the skull will be substantially equal to the diameter of the pin 26 (and thus substantially equal to the length of the tip of the drill bit 27 when it contacts the drill stop contact surface 24).

A second approach to controlling the forward motion of the drill bit allows the surgeon to sense when the bit has passed through the skull in addition to sensing when torque increase as the bit breaks through the skull. The second approach reduces the risk that sensing a change in torque may not always be reliable. It may be difficult to sense torque if the available electric drill lacks speed control or if the patient's skull might be expected to be abnormal. The single pin 26 is replaced by a number of removable clips such as a C clip 90. As seen in FIG. 1e, the drill guide 21 has a thin cylinder rising above it to form a sleeve 29. As seen in FIGS. 1f and 1g, the C clips can be snapped around the sleeve. Each sleeve is in essence a contact surface in addition to contact surface 24. The C clips are about 1 mm in thickness. If the surgeon's best estimation as to where to set the drill stop is three mm above the actual bottom of the skull, the drill bit can be allowed to advanced in a step wise fashion until the drill passes through the skull, The distal end of the drill stop has an enlarged cylinder 92 and enlarged feet 94 to be compatible with the C clip design. A second approach is to have a threaded section on the distal end of the drill stop. Surgeon turns threaded part. 1 turn=1 mm advance.

Bone Collection.

With continuing reference to FIGS. 1a and 1b, a collection container 11 is positioned below the tripod top surface. It has an auger tube 10 at its distal end. The diameter of the tube 10 is about 0.005 of an inch larger than the 0.25-inch drill bit. 27. The clearance between the auger tube 10 and the drill bit 27 is sufficient to cause the drill bit flutes and tube 10 to act as an auger. The auger tube 10 lifts a bone material 14 produced during the drilling process up and into the collection container. 11. The collection process eliminates the need to remove bone material from around the hole that might fall into the drill hole. A yoke 9, shown in FIG. 1b, is an integral element of the tripod. A spring 16, residing between the yoke and the collection container, keeps the tip of the auger tube in contact with the skull as the drill advances into the skull. As shown in FIG. 1d, the collection tube has a container guide slot 18 that slides in a tripod guide bar 20. It keeps the collection container attached and aligned with the tripod.

Catheter Guide.

FIGS. 2a and 2b show a catheter guide 34. The scalp is retracted and a hole is drilled through the bone using the tripod previously described. The anatomy of the head is such that the axis of the drill guide and the axis of the drill hole intersect a ventricle 31. The catheter guide is inserted into the drill hole and held in place by the interference between the bone hole and the body of the guide. A flange 37 on the catheter guide is seated against the skull. The flange stops the movement of the guide into the hole and also tends to square the axis of the guide 34 with the axis of the drilled hole. A ventricular catheter 40 inserted into the guide 34 will be aimed directly at the target ventricle 31. After the catheter is in place within the ventricle 31, the guide is removed from the hole. The catheter is then removed from the guide through an exit slot 36.

Insert Assembly.

FIGS. 3a-c show an insert assembly 2. The basic element of the assembly is an insert body 60 with an insert o-ring 59 and a bolt clamp 66. As shown in FIG. 3c, a catheter pigtail 63 is adhesively attached within a catheter port 62 of the insert body. The proximal end of the pigtail 63 is terminated by a Toughy-Borst fitting 65. A probe pigtail 64 is adhesively attached within a probe port 61 of the insert body. The proximal end of the pigtail is terminated by a luer fitting 75. A guide tube 68 is bonded into the bottom of the probe port. As will be described later, a guide tube 68 is used to direct a monitoring probe into the brain.

Catheter Assembly.

Figure 5H:
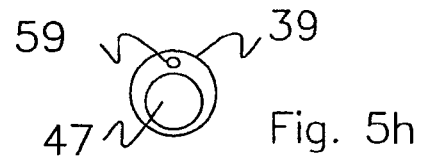
FIG. 5h shows the cross section of a typical two-lumen extrusion.
Figure 5F:
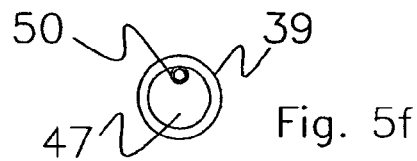
FIG. 5f shows the air tube running inside the lumen of the catheter.
Figure 5C:
FIG. 5c, which is section 5c, shows a bladder in the cage in its curved shape.
Figure 5D:
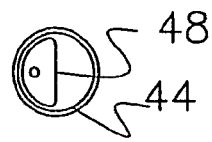
FIG. 5d, which is section 5d, shows a D shaped bladder mount positioned against the cage wall.
Figure 5E:
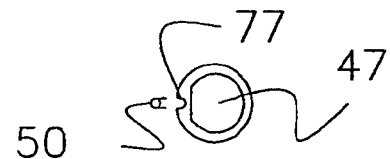
FIG. 5e, which is section 5e, shows a U shaped channel in the catheter body and the air tube that is placed therein.
Figure 5A:
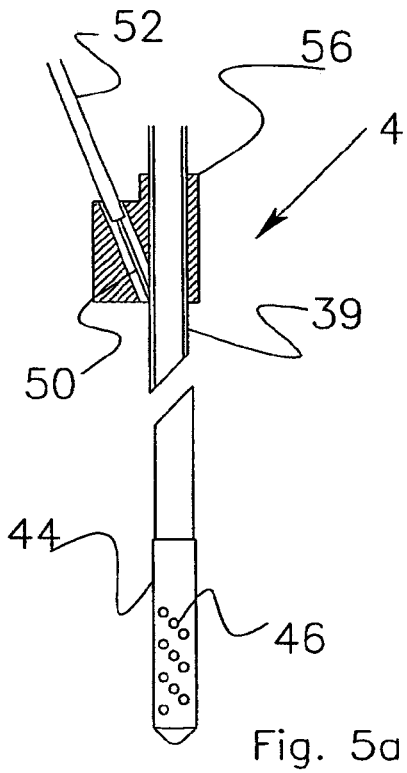
FIG. 5a shows a bladder within a perforated cage situated at the distal end of the catheter and shows a co-extensive placement of an air tube within the catheter wall.

A catheter assembly 3 consists of the insert assembly 21 plus a catheter subassembly 4, which is shown in FIG. 5a. The catheter subassembly 4 will be described later. As shown in FIG. 3c, the insert assembly 2 is assembled with a ventricular catheter 40 at the factory. The surgeon places the combined catheter 40 and insert assembly 21 into a ventricle with the assistance of a stylet 57. The surgeon then moves the insert assembly 2 down the catheter and into a bore 82 of a bolt 80, shown in FIG. 3d. The insert o-ring forms a seal between the insert 2 and bore 82. The bolt clamp 66 engages a capture lip 84 and fixes the insert assembly 2 to the bolt 80. The final configuration of the catheter 40, the insert assembly 2 and the bolt 80, is shown in FIG. 3e.

Probe Insertion.

A principal function of the invention is to facilitate the placement of monitoring probes into the brain. As shown in FIGS. 4a and 4b, the probe pigtail 64 and guide tube 68 provide an access path to a brain 120. An introducer 130 carrying a probe 86, shown in FIG. 4a, is inserted through this access path. The introducer, the probe and its sensor will be described later.

Some probes are sensitive to the nature of the tissue in which they are placed. In order to get an accurate reading, the distal tip of such probes must be placed in tissue that has not been disturbed by the nearby passage of a catheter. A ventricular catheter 40 shown in FIG. 3c, when placed down the bolt 80, disturbs the tissue near the tract through which it passes. A sensitive probe must therefore be directed off to one side. FIGS. 4a and 4b describe the elements involved in two designs that direct the introducer carrying a probe away from the axis of the bolt down which a ventricular catheter has been placed.

In the first design, the introducer 130 is directed away from the ventricular catheter 40 by an elbow 72 shown in FIG. 4d. The elbow 72 is formed in the distal end of the guide tube 68. The displacement of the introducer 130 from the track of the ventricular catheter 40 is indicated by dimension A.

FIG. 4b shows a second scheme, which involves the use of a precurved introducer 131. In this design, the introducer 131 is precurved to a defined radius. The introducer 131 is passed down the guide tube 68. The guide tube 68 straightens the introducer 131 until it exits the distal end of the guide tube 68. At that point, the memory of the introducer curve causes the introducer 131 to follow an arced path that moves it away from the track of the ventricular catheter 40. The displacement distance is again represented by A. The precurved design requires a feature that prevents the possibility of the curved introducer 131 rotating in brain tissue. As shown in FIG. 4c section 4c-4c, the introducer 131 and pigtail 64 in one design have a D cross section. The shape of the two parts prevents the introducer 131 from rotating within the pigtail 64.

A second approach to preventing rotation of the introducer in brain tissue is shown in FIG. 4e. In this approach, the cross section of both the introducer 130 and pigtail 64 are circular. A collar-with-a-pin 160 is bonded to the probe pigtail 64. Once the insert 2 has been placed in the bolt 80, the pin 160 is snapped into a socket 162 molded into the bolt 80. The pin-in-socket fixes the probe pigtail 64 and prevents rotation about its vertical axis or twisting about its horizontal axis.

Catheter Subassembly.

Figure 5B:
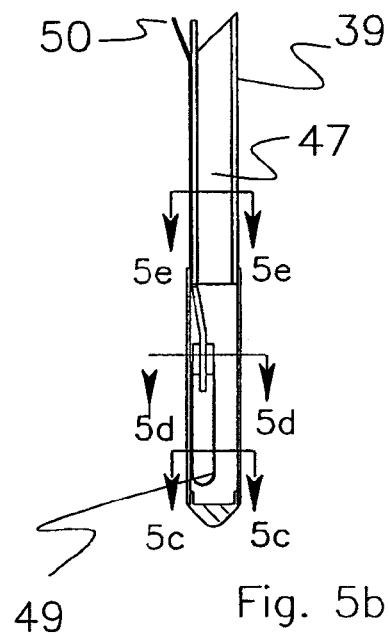
FIG. 5b shows a cross section of the catheter and cage particularly showing the disposition of the bladder and the air tube.

As shown in FIGS. 5a and 5b, a catheter sub assembly 4 consists of a catheter body 39, a bladder cage 44 with radial holes 46 that perforate the cage wall in rows and columns. As shown in FIG. 5b, a bladder 49, section 5c-5c, FIG. 5c, is placed on a bladder mount 48, section 5d-5d, FIG. 5d. An air tube 50, section 5e-5e, FIG. 5e, is inserted into the bladder mount 48. It is placed in a U channel 77 moulded into the wall of the catheter body 39. The air tube extends along the length of the catheter until it exits near its proximal end. The air tube 50 is connected to a more robust air tube extension 52 in a bifurcation 56 to make a kink resistant design. The catheter diameter is reduced by using a separate tube as the air column rather than using a second lumen of a catheter extrusion. The air tube 50 has a thin 0.0015 inch wall, which serves to minimize the catheter OD. As shown in FIG. 5f, the air tube 50 could also be positioned within the catheter lumen 47 of a catheter body 39. The placement of the air tube in a U channel or within a lumen can be applied to a catheter with either an internal or external bladder. FIG. 5g shows a catheter with a bladder 20 mounted on the exterior surface and an air tube running within the lumen. The air tube 50 passes through a hole 58 in the catheter wall located within the confines of the bladder 20. FIG. 5h shows the cross section of a conventional two lumen extrusion. It consists of a catheter body 39, a large lumen 47 and a small lumen 59. A comparison the extrusion of FIG. 5h with the single lumen catheter of FIG. 5f or the dual lumen catheter of 5h shows the larger area of plastic material required to form a dual lumen extrusion. The more material-efficient construction of the single lumen catheter and tube makes it possible to reduce the diameter of the catheter used in the ICP application from a 8.5 Fr to a 7.5 Fr. catheter. The catheter with the U channel shown in FIG. 5e is slightly more efficient than the air tube within the lumen construction shown in FIG. 5f.

As will be discussed, the placement of the bladder 49 in a cage 44 accomplishes three of the inventions objectives. It minimizes the diameter of the catheter body 39, makes possible the placement of a bladder 49 within a catheter that is small in diameter and provides a drainage capability similar to that of standard ventricular catheters. The cage 44 is bonded to the end of the catheter body 39. The bladder 49 is placed on a bladder mount 48. The mount 48 is D shaped to move it to the side of the drainage lumen and to thereby provide a drainage channel that, at its minimum dimension, is similar to the passage way provided in a standard catheter. The minimum dimension is important in that it defines the size of blood clots that can pass through the drainage lumen.

The catheter body 39 is made of polyurethane. The bladder cage 44 is made of a thin wall polyimide tube. The use of polyimide provides a 7.5 Fr. catheter with a larger ID than would be the case if the cage segment were polyurethane. The larger ID makes it possible to house the bladder 49 within the catheter and achieve a minimum flow path dimension, all within a catheter diameter similar to the standard drainage-only ventricular catheters now used. The wall thickness of the polyurethane catheter is 0.10 inch. The wall thickness of the polyimide cage is 0.002 inch. The use of polyimide increases the ID of the segment of the catheter in which a bladder mount 48 and a bladder 49 are located. The difference in the thickness between the polyimide and urethane walls amounts to 0.016 inches (0.02-0.004), which is equal to 1.2 Fr. The catheter body is 7.5 Fr. An all-polyurethane catheter would have to be almost 9 Fr. to provide the same internal diameter as the polyimide cage. The use of a polyimide gage is thereby an important element in achieving the objective of minimizing the diameter of the catheter.

Drainage Capability.

The polyimide tube also increases the drainage capability of the catheter. As shown in FIGS. 5a and 5b, radial holes 46 pass through the cage 44 wall and allow cerebral spinal fluid (CSF) to enter a drainage lumen 47. The thin wall and the strength of polyimide make it possible to drill closer spaced radial holes than would be the case with a polyurethane catheter. The increase in hole count thereby provides a larger total cross section of radial holes leading to the central drainage lumen of the catheter. Four rows with 8 holes per row are drilled into the cage for a total of 32 holes. Each hole is 0.9 mm in diameter. A standard ventricular catheter typically has 10-15 1 mm holes. A prior art air-column catheter has 4 radial holes. The close spacing allowed by the use of a thin wall rigid polyimide tube makes it possible to present a larger radial hole flow path than is practical in the thicker wall of a flexible polyurethane or silicone catheter. The polyimide cage 44 with the hole count as presented herein has 2 times the total radial hole diameter of a standard catheter and 8 times the radial hole area of a prior art air-column catheter.

Small Diameter Catheter.

A bladder 49 functions within the polyimide cage 44. When collapsed by ICP, the bladder 49 goes from its normal cylindrical shape to a flat shape. A bladder 49, when flattened, is 1.5 times as wide as the diameter of the cylinder prior to flattening. In order to use a small OD cage, the bladder 49 is caused to assume a C shape. A 0.070 diameter bladder 49 is used in the design. The bladder's flattened width is 0.110 inch. The bladder 49 is placed in a cage 44 with an ID of 0.098 of an inch. When collapsed by ICP, the bladder 49 assumes a C shape with a radius of slightly over 0.2 inch. In order to function while in a C shape, the bladder material, bladder wall thickness, bladder volume and volume of injected air must be closely controlled. A relative thick wall or excess of injected air will prevent proper operation of a C shaped bladder. An example of a bladder with the requisite characteristics is a 0.55-inch long bladder 0.070 inches in diameter having a 0.003 thick wall made of butyl rubber. The volume of air injected is limited to 10 ul.

The shape and location of the mount 48 upon which the bladder 49 is placed is an important element in integrating the various functions of the catheter into a small diameter catheter. As shown in FIG. 5b, section 5d-5d, a bladder mount 48 has a reversed D shape and is positioned against the side of the polyimide tube 44. The mount shape and placement allow the most narrow drainage passageway in the inner lumen to be similar to the diameter of the drainage lumen of a standard ventricular catheter. The ID of the polyimide tube is 0.098 inches. The width of the D is about 0.045 of an inch. The thickness of bladder wall is 0.003. The width of the bladder and mount is 0.051 of an inch. The clearance between the mount and the 0.098 ID cage wall is therefore about 0.047 of an inch. If a conventional cylindrical shaped bladder mount were used and placed against the side of the cage, the minimum clearance would be decreased from 0.047 of an inch to 0.025. A catheter with a center positioned bladder would have to be 2 Fr. larger in diameter than the present design to provide a minimum clearance of about 0.050 of an inch. The use of a D shaped bladder mount and a bladder that can operate in a C shape are important design elements in achieving a small diameter catheter that offers a standard drainage capability.

A fourth design element also contributes to achieving a small diameter catheter. Heretofore, a second lumen has been used as the air column between the bladder and a transducer. In the present invention, a separate tube is used as the air column. As seen in comparing the typical cross section of the two lumen extrusion in FIG. 5h with a separate tube construction of either FIG. 5e or FIG. 5f, a separate tube substantially reduces the amount of plastic material used. In the case of the ICP catheter, the separate tube design requires the use of ⅓ less material than the two lumen extrusion. The reduction in material usage can be used to effect a proportional reduction in catheter diameter or can be used to increase the diameter of the non air column lumens. A smaller diameter catheter has merit in an ICP application and is of value in any catheter introduced into the body. It is of particular merit when catheter diameter affects its intended function such as in a urodynamic catheter that measures the constrictive profile of the urethera. In the urodynamic application, the more optimal use of space can be used to reduce the catheter diameter or increase the diameter of the filling lumen. In the ICP catheter application, the air tube 50 is isolated from a drainage lumen 47 by placing it in a channel 77 formed in the exterior of the catheter. The external placement keeps the air tube from being randomly disposed with the drainage lumen where it might interfere with the passage of material entering the drainage lumen. As shown in FIGS. 5a and 5b, an air tube 50 extends from the bladder mount 48 to the proximal end of the catheter. As shown in FIG. 5e section 5e-5e, the catheter body extrusion 39 has a U channel 77 in the sidewall. The wall of the catheter can be quite thin at this point since the air tube 50, when potted into the U channel 77, more than matches the strength of the normal wall thickness. The air tube 50 exits the cage directly below the U channel 77 in the catheter wall and is placed in the U 77, where it runs up the side of the catheter As seen in FIG. 5a-b, the air tube 50 coextends along the length of the catheter to about 1 inch from the catheter's proximal end. At that point it enters an air tube bifurcation 56 where the catheter and air tube 50 are separated. The air tube 50 is joined to an air tube extension 52 within the bifurcation 56. The air tube extension 52 has sufficient wall thickness to resist kinking forces that may be encountered proximal to the bifurcation 56. The air tube extension 52 connects to a piston, which, in combination with a transducer housing, injects the requisite amount of air to enable the bladder to operate as described in U.S. Pat. No. 5,573,007, the entire contents of which is hereby incorporated by reference.

In summary, the insert assembly consists of an insert body that holds a catheter pigtail, two probe pigtails, two guide tubes, a sealing o-ring and a bolt clamp that secures the insert to the bolt when the clamp engages the capture lip of the bolt. The catheter assembly consists of a catheter body, a thin wall cage that holds the bladder on a D-shaped bladder mount and provides a large number of radial holes that feed the drainage lumen. The air tube is held in a channel that runs along the outside of the catheter.

Probe Placement.

Figure 6A:
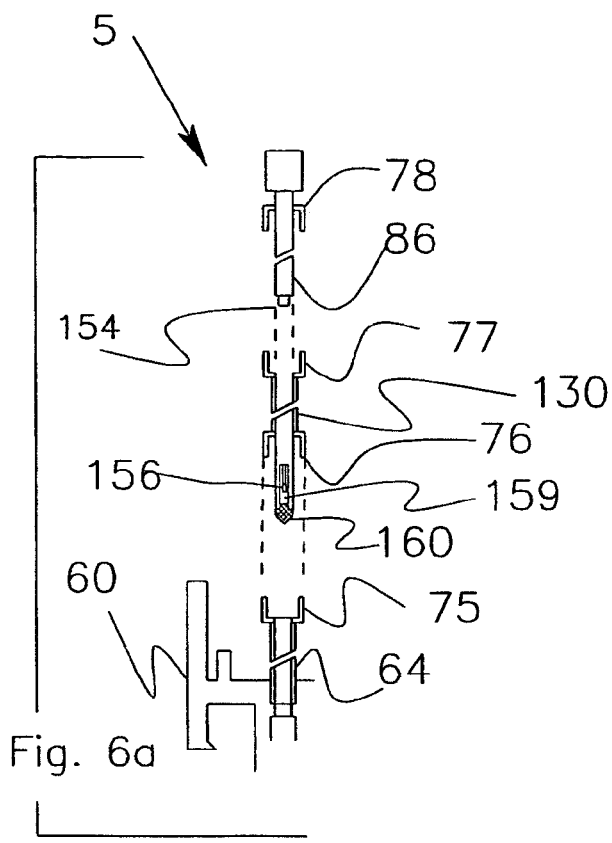
FIGS. 6a-e shows the incorporation of a temperature sensor into the introducer, particularly showing the placement of the sensor wires on the outside of the catheter.

The sensor of some monitoring probes is placed in a soft, highly flexible tube. Such a probe may be unable to be redirected into undisturbed tissue as it can neither interact with a deflector nor can it be precurved. The present invention provides the properties necessary to locate such a probe in undisturbed tissue by inserting it into an introducer. The introducer can be made stiff enough to be directed by a deflector or can be imbued with a memory to produce a precurved introducer. As shown in FIG. 6a an assembly 5 consists of a probe, an introducer and the pigtail to which the introducer is attached. A probe 86 has a luer connector 78. The probe is inserted into an introducer 130. The introducer has a luer fitting 77 on the proximal end as well as a luer fitting 76 located about 1 inch from the proximal end. The probe 86 is inserted into the introducer 130 until its luer 78 encounters the proximal luer 77 of the introducer. The luers are mated. The introducer 130 is then inserted into the probe pigtail 64 and advanced until a luer 76 of the introducer 130 can be joined to a luer 75 of the pigtail 64. The probe 86 can be placed in the brain at any depth desired by varying the location of luer 76 and the length of the probe pigtail 64.

The introducer is filled with water before the probe is inserted. The water displaces air that would otherwise be present in the annulus between the probe and introducer ID. The removal of air assures that the oxygen sensed by the probe will be that of the brain and not that of entrapped air.

Introducer with a Temperature Sensor.

Figure 6E:
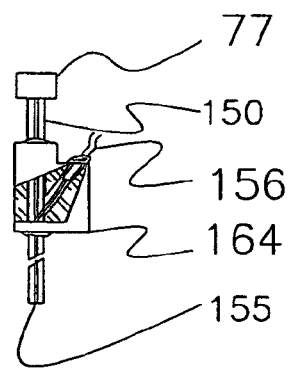

The two most used probes at this time are oxygen and temperature. Temperature is required to interpret the oxygen signal and is therefore very commonly used. At times, there is a need to place more than two probes into the brain such as a flow probe or a dialysis probe. One solution to the access problem, of course, would be to provide additional probe ports by using a larger bolt, which would then require a larger diameter hole in the skull. Rather than increase the bolt diameter, the present invention frees up a port by incorporating a temperature sensor 155 into the introducer 130 as shown in FIG. 6b. The guide tubes 68 are designed to accept an introducer 130 with a diameter of about 0.050 of an inch. An introducer lumen 154 receives a probe 86 that is about 0.030 of an inch in diameter. The available wall cross-section area is therefore very limited. The thermocouple wire used for temperature measurement must be of a small diameter of about 0.003-0.005 of an inch. Referring to FIG. 6b, a sensor wire set 152 is placed in a U channel 89 that extends the length of the catheter to a bifurcation 154 shown in FIG. 6e. The wire set 152 is joined to a large diameter wire 156 within the bifurcation. The larger diameter wire 156 is sufficiently rugged to extend from the catheter to an instrument. The sensor 155 and wires 152 are placed in the channel 89 and potted in place with UV adhesive. The concept of running a second function up a channel in the side of the catheter rather than through a second lumen was discussed earlier. In the case of the introducer 130, an approach wherein a second lumen is used to string the wire from the proximal to distal end would make assembly difficult. The second lumen diameter would be less than 0.010-inch diameter. Piercing such a hole in the wall of such a small lumen and stringing wire through it and down a lumen presents a difficult fabrication problem. The concept of running a wire up an exterior channel is valuable in that it both minimizes the catheter OD and reduces the cost of fabrication.

Figure 6D:
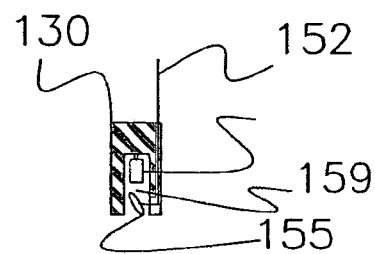
Figure 6B:
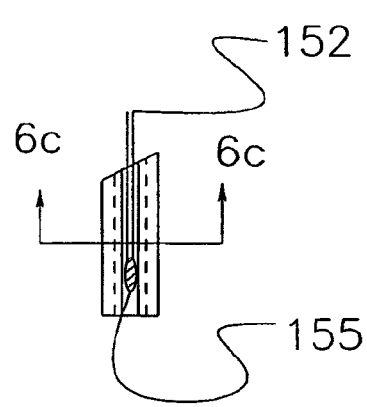
Figure 6C:
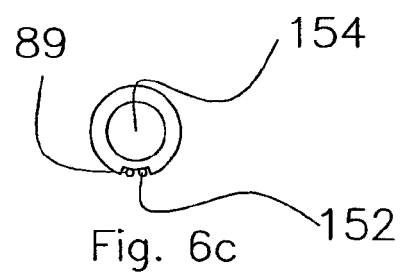

In the case where a sensor may be too large to fit in the narrow channel 89, the sensor can be positioned within the lower portion of the side window 159 as shown in FIG. 6d. In this arrangement, the channel need only accommodate the sensor wire or fiber optic. The potting material used to secure the sensor in the window has been omitted from the drawing for sake of clarity. If the sensor is a light based sensor, such as one using an LED, the potting material must be transparent. If it is not an optical sensor, the sensor can be potted in place with any biocompatible adhesive. Since the parameters measured by sensors change slowly within the brain, the reduction in response time due to sequestering the oxygen probe or temperature probe within the introducer will not affect the utility of the sensor.

OPERATION OF THE INVENTION

Bone Collection

The hole drilled in the skull to gain access to the brain produces a quantity of bone material that piles up around the drill hole like an anthill. The skull may be 0.25-75 inches deep, therefore the amount of bone material created can be substantial. In the prior art, the bone material is removed by a combination of swabbing and flushing. Some of the bone material falls back into the hole in the cleaning process. Removing the bone material takes time and contaminates the operation site. The present invention creates a bone collection system by creating an auger that consists of the flutes of the drill bit and a surrounding tube. The bone material is carried up the auger and deposited in a collection container. It is important that the tube stay on the skull so the bone material cannot escape through a gap between the tube and skull. The bone container is therefore spring loaded against the tripod to which it is mounted. The surgeon normally uses a hand drill to drill a hole. Both hands are occupied in this process. In the present invention, an electric drill is used, which only requires the use of one hand thus freeing the second hand to hold the tripod in place.

Precise Drill Stop.

A skull hole is usually drilled with a hand-operated drill. The limitations of present drill stops are such that a simple electric drill is not used. If the drill bit is driven by an electric drill, the momentum of the motor can be such that the spiral flutes will pull the drill down into the brain once the body of the bit exits the skull. The availability of an improved drill stop that would make it possible for an electrical drill to be used would be an important improvement. It would remove the risk that the bit might be pulled into the brain, reduce the time required to drill the hole and free a hand to make possible the use of tripod described earlier. At present, the surgeon sets the drill stop so it will stop the bit short of the estimated thickness of the skull. The setting is imprecise since the surgeon does not know the exact thickness of the skull. When the drill stop encounters the skull, the drill stop is untightened. The surgeon then proceeds cautiously until it seems that the drill bit has passed through the skull. It is difficult to sense when the drill is just about through the last segment of the skull. It is therefore likely that the bit will either stop short of full penetration or will pass below the skull some distance. A premature stop will leave a bone edge sticking out that may damage sensors inserted through the hole. Passage of the drill bit into the dura will push will either tear it or push it away from the skull and cause bleeding.

The present invention enhances the traditional drill stop by adding a precision stop feature. It differs from a standard drill stop in several ways. A normal drill stop stops when it contacts the skull. There is no room for a second element to provide a more precise stop. In the present invention, the drill stop operates above the skull. By controlling the stop above the skull, it is possible to add an element that precisely controls the depth of the drill. The torque required to turn the drill increases when the tip of the drill bit passes through the skull. The surgeon, sensing the high torque event, stops drilling at this point, moves the drill stop down to the pin and tightens it. He then pulls the pin on the top of the drill guide at which point he can resume drilling with the assurance that the drill bit will stop as soon as it has traveled a length equivalent to the diameter of the pin, which is a distance equal to the length of a drill bit tip. A more conservative precision drill stop can be made by placing a number of C clips 90 on a smaller diameter segment 29 of the tube guide 21 (See FIG. 1f). The drill stop ID 92 is increased to allow ingress of the smaller diameter segment. A flange 94 is placed on the distal end of the drill stop. It stops the drill stop when it reaches a contact surface. The drill stop designs discussed allow the forward motion of the drill bit to proceed in small well controlled steps. Several other methods of precisely controlling the forward motion of the drill bit can be envisioned such as a threaded distal end of a drill stop that has a nut wherein the position of the nut defines the allowable forward motion of the drill stop.

The system has several advantages other than precisely stopping the bit after the body passes through the skull. An electric drill is fairly stable and is not subject to the wobble introduced by a hand turned bit. The wobble tends to produce a conical hole until the bit has entered the bone to some extent. The conical shaped hole reduces the effective length of the threaded section of the bolt, which makes for a less well-anchored bolt. The use of an electric drill also frees one hand to hold the tripod in place.

In order to assure proper control of the drill, a driver is chosen that has a rotational speed of about 200 rpm, is light in weight and is limited in its torque capability so it grabs and stops when it hits the high torque event associated with the point of the drill passing through the skull. The appropriate weight and torque capability will vary with the diameter of the hole, but the appropriate combination can easily be determined empirically for any given drill diameter.

Catheter Guide.

Head trauma treatment frequently involves placing a ventricular catheter into a ventricle within the brain to provide a means of removing cerebral spinal fluid (CSF) and thereby increase the volume within the skull into which swollen brain tissue can move. The placement procedure involves aiming a catheter down an oversized drill hole and moving it toward the brain at an angle that will hopefully intercept the targeted ventricle. The patient is usually lying on a bed tilted to a 30-degree angle. The head is an irregular shaped object. Given the head's angle, the lack of simple guidance landmarks and the fact that the procedure is infrequently done by most neurosurgeons, the placement procedure is difficult. It is not uncommon to miss the ventricle and to therefore have to try again. The present invention assists in placement by closely controlling the angle of entry of a ventricular catheter. It does so by first drilling a hole with an axis that intercepts the target ventricle. The orientation of the hole is accomplished by using a tripod 28 with its drill guide 21.

The tripod provides the ability to orient the axis of a drill hole. It is well understood that an imaginary line perpendicular to the surface of the head will intercept a ventricle in the brain. The planer surface joining the legs of a tripod is parallel to the skull. The axis of the guide tube 21, which is perpendicular to the planer surface, therefore intercepts a targeted ventricle. The guide tube orients the drill bit and causes it to drill a hole whose axis passes through a ventricle. A catheter guide 34 is placed in the oriented hole and its flange seated against the skull. The guide presents a long small diameter aperture that closely defines the angle at which the ventricular catheter enters the brain. The use of an aligned catheter guide with an elongated small aperture greatly increases the likelihood of successful placement.

Therapy: A Catheter with a Standard Drainage Capability.

A principal function of a ventricular catheter is that of draining CSF. It is not uncommon for the drainage function of the catheter to be disabled by blood clots or brain tissue that clog the radial holes leading to the central drainage lumen.

The design of prior art air-column ventricular catheters is such that their drainage capability is compromised. The bladder used is a sleeve bladder. The tubular sleeve is slipped on the catheter, and then both ends of the sleeve are joined to the catheter body. The length of the bladder required in the prior art system is such that most of the length of the catheter that might reside in a ventricle is covered by the bladder. Consequently, the distal end of the catheter has but 4 radial holes that lead to the drainage lumen. A standard ventricular catheter, in comparison, has 10-16 holes.

The present invention uses a small bladder that can be placed inside the catheter. The entire body of the catheter is therefore available for the placement of radial holes near the distal end. The design has a second element that further increases the drainage capability of the catheter. Standard catheters are made of silicone or urethane that have a thick wall so the tube will not kink when subjected to bending forces when outside the skull. The body of the catheter of the present invention is also urethane for most of its length. The distal end wherein the radial holes are placed is made of polyimide, a somewhat rigid material. The material properties are such that holes can be more closely drilled than is the case with polyurethane. The present invention capitalizes on the material properties by providing, in a preferred embodiment, 32 laser drilled radial holes. The drainage capability is therefore about 8 times that of the prior art air-column catheter. The likelihood that material may become logged in a radial hole is also reduced in that the length of the radial hole is reduced from 0.01-0.02 inches to 0.002 inches. The shorter hole of the polyimide tube is less likely to become plugged by incoming material than the longer hole of a standard catheter.

Standard Catheter Diameter.

Standard ventricular catheters are about 7 Fr. in diameter. Catheters with a built-in pressure sensor are 9-10 Fr. in diameter. Obviously, a smaller diameter catheter is to be preferred to a larger diameter catheter. An objective of the present invention is to provide a multi-sensor catheter that is approximately the same size as the standard drainage-only catheters. One of the principal requirements of any drainage catheter is that the main drainage lumen be larger than the radial holes that feed it. The larger diameter drainage lumen makes it likely that anything passing through the radial holes will pass through the main drainage lumen. A standard ventricular catheter has an ID of 0.052 inches. One objective of the present invention is to produce a catheter that has a minimum passageway of about 0.050. The bladder used is 0.070 inches in diameter, which is about as small a diameter as it practical to make and assemble. The bladder must be mounted on a bladder mount. A combination of three design concepts makes it possible for the drainage lumen to have a minimum passageway of about 0.050. The first concept is that of placing the bladder in a polyimide cage rather than in the body of the urethane catheter. Because of its strength, the wall of the polyimide cage can be quite thin, in this case, 0.002. A polyurethane catheter wall, in contrast, needs to be 0.010. The two walls of the polyimide tube total 0.004 inches vs. 0.020 inches in the case of a polyurethane catheter. Placing the bladder in a polyimide cage rather than a polyurethane tube reduces the diameter of the catheter by 1.2 Fr. sizes.

A second concept that affects the diameter of the catheter is the shape of the bladder mount. Rather than mount the cylindrical bladder on a cylindrical mount, the bladder is mounted on a D shaped mount. The mount and its bladder are moved against the inner wall of the cage to thereby present the maximum clearance between the cage wall and the bladder mount. As described earlier, a D shaped mount placed at the side of the catheter allows the bladder to function in a catheter 2 Fr. sizes smaller than would be the case if a cylindrical mount were used. The third concept that affects overall catheter diameter is that of isolating the air tube from the drainage lumen. The air tube must be prevented from running through the drainage lumen, as a random placement will reduce the minimum passageway dimension. The conventional approach used to isolate a second function, such as the air tube, is to provide a catheter with a second lumen. The present design minimizes the diameter of the air tube by placing a thin wall polyimide tube within a U shaped channel formed in the outer wall of the catheter. The U channel runs up the side of the catheter. The thin wall air tube has a 0.0015 inch thick wall. If housed in a supporting U shaped channel, the physical properties of the thin wall polyimide are adequate. The wall thickness of an air tube made of conventional materials such as polyurethane or nylon tube would be about 0.01 inches thick. A catheter using conventional materials would therefore be larger in diameter.

External placement of the polyimide tube eliminates the need for a second lumen and thereby eliminates the thickness of the septum wall required to form a second lumen. The thin wall polyimide tube is incapable of withstanding kinking forces encountered once it exits the catheter. The tube is therefore joined to a more robust tube in a bifurcation fitting located at the proximal end of the catheter.

The external placement of the air tube provides another benefit. It eliminates the need to perforate the catheter wall to gain access to a second lumen. The cost of potting the air tube in the catheter channel is somewhat less expensive than the process involved in perforating the catheter wall and inserting the tube within the second lumen. The reduction in cost provided by running a second catheter function in a channel in the side of the catheter increases as the diameter of the second lumen that would otherwise be required decreases. The cost benefit is particularly important in small catheters as will be discussed later when describing an introducer with a temperature sensor.

Introduction of Several Monitoring Probes.

The care of certain patients who have undergone brain trauma has changed in the recent past. Until recently, the only devices placed in the brain were an intracranial pressure sensor (ICP) or a combination ICP sensor and drainage catheter. Recently, surgeons have desired the placement of an oxygen sensor and a temperature sensor. A temperature sensor is required, as the oxygen signal must be interpreted as a function of temperature. Other probes are being placed in experimental work and may well become a standard of care. The probes include blood flow and dialysis devices.

The only prior art device now available for measuring oxygen has a bolt and guide tube system that have the ability to accept an ICP sensor, an oxygen sensor and temperature sensor. It cannot, however, pass a drainage catheter. A drainage capability is provided by drilling a second hole in the patient's head and placing a catheter in a ventricle through the hole. The matter of adding a ventricular catheter to a three-parameter system must deal with the fact that an oxygen probe must be placed in undisturbed tissue to provide a correct reading. The prior art device, which consists of three parallel guide tubes aligned with the axis of the bolt, isolates the oxygen probe by placing it down its guide tube to a deeper level than the temperature and ICP sensors. This strategy cannot be used if a ventricular catheter is to be passed down the bolt as the catheter extends from the skull to a ventricle. The track of the catheter nearly parallels the axis of the bolt. An oxygen probe placed straight into the brain would encounter disturbed tissue. The present invention provides a capability to insert an ICP sensor, an oxygen sensor, a temperature sensor and a drainage catheter through one hole and to do so in a manner that locates the oxygen probe in undisturbed tissue. The system consists of a bolt that is screwed into a skull hole and a catheter that can measure ICP and drain CSF. A plastic part, an insert assembly 2, has two pigtails through which probes may be inserted and two guide tubes that guide probes into the brain. The insert is placed on the catheter at the factory. As soon as the ventricular catheter is inserted into the brain, the insert is moved down the catheter and placed in the bore of a bolt that has been screwed into the skull hole.

The oxygen probe is moved away from the track of the catheter into undisturbed tissue as it is introduced into the brain. The present invention describes two designs that move the probe away from the catheter track. Either design can be used with an introducer 130 or 131. The introducer provides a consistent pushability characteristic to probes that may be used. In one design, a guide tube 68 has an elbow at its distal end. The elbow causes the introducer to exit the guide tube at an angle roughly of 30 to 45 degrees. In a second design, the introducer is precurved. After it passes through the guide tube, the memory of the introducer causes the introducer to follow a curved track through the brain. The introducer of the precurved design can be prevented from rotating about the bolt axis by either one of two approaches. In one approach, the pigtail and introducer are D shapes or elliptical so the introducer cannot rotate within the pigtail. In a second design, a pin-with-a-collar 160 is bonded to the probe pigtail. The collar has a pin that can be snapped into a socket 162 molded into the wing of the bolt. The collar prevents the pigtail from moving.

The depth to which the probe is inserted can be controlled by varying the length of the probe pigtail, the length of the introducer and the location of the mid luer on the introducer. The system can thereby be tailored to be used with any probe.

Introducer with a Temperature Sensor.

Although oxygen and temperature are the most commonly used probes, blood flow sensors and dialysis probes are being placed in some patients. The bolt and insert of the present invention are designed to receive two probes. Although a third probe port could be added by increasing the diameter of the bolt and adding a third probe port to the insert, a preferred approach is to place the oxygen and temperature sensor in one introducer and thereby make a second probe port available without increasing the size of the drill hole. In order to fit a temperature sensor within the limited cross sectional area of the introducer and as a means of keeping the cost of manufacture down, the temperature sensor and its wires are placed in a U shaped channel that runs the length of the catheter. The oxygen sensor is placed in the main lumen. The sensor and wires or fibers of the temperature sensor run within the channel. The sensor is bonded at the distal end of the introducer within the channel if it is small enough in size to fit. If it is too large, the sensor is placed within the window 159 in the distal tip of the introducer as shown in FIG. 4d.

It is understood that the preceding description is given merely by way of illustration and not in limitation of the invention and that various modifications may be made thereto without departing from the spirit of the invention as claimed.

What is claimed is:

1. A method of placing a probe at a target location of a patient's cranial space comprising:
    creating an access hole in a cranial bone of said patient;
    placing a probe platform into said access hole;
    introducing a catheter through a longitudinal first passage of said probe platform and into said cranial space;
    introducing a probe through a second passage of said probe platform and along an axis substantially parallel to said longitudinal first passage;
    advancing said probe past said probe platform and through a straight region of said second passage, continuing along said axis substantially parallel to said longitudinal first passage and towards said patient's cranial space; and,
    upon reaching a curved elbow at a distal end of said second passage, urging said probe away from said axis and said catheter via a distal curved portion of said second passage.

2. A method according to claim 1, wherein the introducing of said probe into said cranial space includes introducing said probe into a guide tube of said probe platform.

3. A method according to claim 2, wherein the introducing of said probe into said cranial space includes introducing said probe into a guide tube wherein a distal end of said guide tube is curved away from said axis.

4. A method according to claim 1, wherein the urging of said distal end of said probe away from said axis includes urging said distal end at an angle of about sixty degrees from said axis.

5. A method according to claim 1, wherein the introducing of said probe through said probe platform includes placing said probe on an introducer and inserting said introducer into said probe platform.

6. A method according to claim 5, wherein the inserting of said introducer includes inserting said introducer having a curved shape at its distal end when in a normal state.

7. A method according to claim 1, wherein said catheter is a drainage catheter.

8. A method according to claim 1, further comprising, introducing a second probe into said cranial space through said probe platform.

9. A method according to claim 1, wherein the introducing of a probe includes introducing an oxygen probe.

10. A method according to claim 9, wherein the target location is undisturbed tissue located in said cranial space.

11. A method of placing a probe at a target location of a patient's cranial space comprising:
- placing a probe platform into an access hole in a cranial bone and into a cranial space of said patient;
- introducing a catheter through a longitudinal first passage of said probe platform and into said cranial space; said longitudinal first passage extending along an axis of said probe platform;
- introducing a probe through a second passage of said probe platform and along said axis; said second passage including a guide tube extending distally from said probe platform and linearly along said axis into said cranial space; and,
- bending said probe away from said axis upon reaching a curved elbow at the distal end of said guide tube and advancing said probe away from said catheter.

* * * * *